United States Patent
O'Donnell

[19]

[11] Patent Number: 5,562,614
[45] Date of Patent: Oct. 8, 1996

[54] PROGRAMMABLE MANIFOLD SYSTEM FOR AUTOMATIC FLUID DELIVERY

[75] Inventor: Joseph A. O'Donnell, Escondido, Calif.

[73] Assignee: Advanced Cardiovascular Systems, Inc., Santa Clara, Calif.

[21] Appl. No.: 156,265

[22] Filed: Nov. 22, 1993

[51] Int. Cl.$^6$ ................................................. A61M 1/00
[52] U.S. Cl. .............................................................. 604/65
[58] Field of Search ................................ 604/97–100, 65, 604/67, 245–246, 250, 80–82, 259, 260, 83, 86, 283, 284, 415, 905, 122–126; 128/DIG. 12, DIG. 13; 137/588

[56] References Cited

U.S. PATENT DOCUMENTS

| | | |
|---|---|---|
| 3,623,474 | 11/1971 | Heilman . |
| 3,698,381 | 10/1972 | Federico et al. . |
| 3,701,345 | 10/1972 | Heilman et al. . |
| 3,720,199 | 3/1973 | Rishton et al. . |
| 3,985,123 | 10/1976 | Herzlinger et al. . |
| 4,006,736 | 2/1977 | Kranys et al. . |
| 4,056,043 | 11/1977 | Sriramamurty et al. . |
| 4,106,002 | 8/1978 | Hogue, Jr. . |
| 4,321,014 | 3/1982 | Eburn, Jr. et al. . |
| 4,332,254 | 6/1982 | Lundquist . |
| 4,370,982 | 2/1983 | Reilly . |
| 4,439,185 | 3/1984 | Lundquist . |
| 4,439,186 | 3/1984 | Kuhl . |
| 4,493,704 | 1/1985 | Beard et al. . |
| 4,576,181 | 3/1986 | Wallace et al. . |
| 4,583,917 | 4/1986 | Shah . |
| 4,583,974 | 4/1986 | Kokernak . |
| 4,608,994 | 9/1986 | Ozawa et al. . |
| 4,610,256 | 9/1986 | Wallace . |
| 4,651,738 | 3/1987 | Demer et al. . |
| 4,654,027 | 3/1987 | Dragan et al. . |
| 4,655,749 | 4/1987 | Fischione . |
| 4,677,980 | 7/1987 | Reilly et al. . |
| 4,677,982 | 7/1987 | LLinas et al. . |
| 4,694,409 | 7/1987 | Lehman . |
| 4,723,938 | 2/1988 | Goodin et al. . |
| 4,743,230 | 5/1988 | Nordquest . |
| 4,758,223 | 7/1988 | Rydell . |
| 4,781,192 | 11/1988 | Demer . |
| 4,795,431 | 1/1989 | Walling . |
| 4,796,606 | 1/1989 | Mushika . |
| 4,808,165 | 2/1989 | Carr . |
| 4,832,692 | 5/1989 | Box et al. . |
| 4,838,864 | 6/1989 | Peterson . |
| 4,854,324 | 8/1989 | Hirschman et al. . |
| 4,858,615 | 8/1989 | Meinema . |
| 4,911,695 | 3/1990 | Lindner . |
| 4,919,121 | 4/1990 | Rydell et al. . |
| 4,929,238 | 5/1990 | Baum . |
| 4,940,459 | 7/1990 | Noce . |
| 4,944,726 | 7/1990 | Hilal et al. . |
| 4,952,928 | 8/1990 | Carroll et al. . |
| 4,985,015 | 1/1991 | Obermann et al. . |
| 5,004,472 | 4/1991 | Wallace . |
| 5,007,904 | 4/1991 | Densmore et al. . |
| 5,009,662 | 4/1991 | Wallace et al. . |
| 5,015,233 | 5/1991 | McGough et al. . |

(List continued on next page.)

FOREIGN PATENT DOCUMENTS

| | | |
|---|---|---|
| WO90/04987 | 5/1990 | WIPO . |
| WO90/11040 | 10/1990 | WIPO . |
| WO92/06735 | 4/1992 | WIPO . |
| WO92/15359 | 9/1992 | WIPO . |

*Primary Examiner*—Manuel Mendez
*Attorney, Agent, or Firm*—Fulwider Patton Lee & Utecht, LLP

[57] ABSTRACT

A programmable manifold system for controlling pressure and fluid delivery within and through a catheter for use in a body lumen is disclosed. By means of a feedback loop controller, the system delivers known volumes of media through the catheter and into the body lumen and the system conforms the rate of change of pressure within the catheter to a desired value and makes possible consistent expansions and deflations using an automated or semi-automated system regardless of variations in catheter volume and compliance characteristics.

17 Claims, 2 Drawing Sheets

U.S. PATENT DOCUMENTS

| | | |
|---|---|---|
| 5,019,041 | 5/1991 | Robinson et al. . |
| 5,021,046 | 6/1991 | Wallace . |
| 5,047,015 | 9/1991 | Foote et al. . |
| 5,057,078 | 10/1991 | Foote et al. . |
| 5,084,060 | 1/1992 | Freund et al. . |
| 5,135,488 | 8/1992 | Foote et al. . |
| 5,152,776 | 10/1992 | Pinchuk . |
| 5,163,904 | 11/1992 | Lampropoulos et al. . |
| 5,201,753 | 4/1993 | Lampropoulos et al. . |
| 5,207,642 | 5/1993 | Orkin et al. ............... 604/65 |
| 5,215,523 | 6/1993 | Williams et al. . |
| 5,273,537 | 12/1993 | Haskvitz et al. . |
| 5,300,027 | 4/1994 | Foote et al. . |

PROGRAMMABLE MANIFOLD SYSTEM FOR AUTOMATIC FLUID DELIVERY

BACKGROUND OF THE INVENTION

This invention relates generally to inflation devices used in medical procedures, and more particularly, to an automated manifold control system suitable for controlling the expansion and deflation of catheter balloons used in procedures within a body lumen such as a blood vessel and for controlling the delivery of desired components to the body lumen that is the subject of the procedure. Such procedures include, for example, vascular procedures such as angioplasty or restoring patency of a blood vessel.

Dilatation balloon catheters have been used in increasing numbers in angioplasty procedures to dilate or enlarge body lumens such as blood vessels that have been partially or almost completely blocked by stenosis. In addition to vascular procedures such as dilatation of the coronary and peripheral arteries, angioplasty procedures have been used to treat stenoses and other lumens, such as urethral passages and fallopian tubes. Particularly, the procedure for dilating coronary arteries, referred to as percutaneous transluminal coronary angioplasty (PTCA), has provided an effective and less traumatic treatment technique than coronary by-pass surgery or other surgical treatment methods.

In a typical angioplasty procedure, a guiding catheter is percutaneously introduced into the vascular system of a patient and is directed to a point near the site of the stenosis. Subsequently, a guidewire and a dilatation catheter having an inflatable balloon on the distal end thereof are introduced through the guiding catheter with the guidewire slidably disposed within an inner lumen of the dilatation catheter. The guidewire is advanced out of the distal end of the guiding catheter and is maneuvered into the patient's vasculature containing the stenosis to be dilated, and is then advanced beyond the stenosis. Thereafter, the dilatation catheter is advanced over the guidewire until the dilatation balloon is located across the stenosis.

Once in position across the stenosis, the balloon of the dilatation catheter is filled with radiopaque liquid at relatively high pressures and is inflated to a predetermined size, preferably the same as in the inner diameter of the artery at that location. The inflated balloon radially compresses the atherosclerotic plaque and/or other deposits comprising the stenosis against the inside of the artery wall to thereby dilate the lumen of the artery and allow blood to flow freely therethrough. In a typical procedure, the balloon is expanded and deflated several times, with the pressure maintained for several seconds during each expansion, until the desired patency in the blood vessel is obtained. To determine whether the desired patency of the blood vessel is obtained, it may be desirable to deliver radiopaque liquid to the repaired site so that, through the use of radiography, the interior profile of the blood vessel can be viewed. It may also be desirable to flush the site with some solution to facilitate a complete repair of the blood vessel or to deliver drugs into the blood vessel. Once the desired patency is obtained and any desired components have been delivered to the blood vessel, the dilatation catheter can be removed.

To expand or deflate the balloon, the physician typically uses a system such as a syringe connected to the catheter and in fluid communication with a lumen leading to the interior of the balloon. The physician uses one hand to grasp the syringe body and the other hand to actuate the plunger to pressurize and depressurize the expansion fluid. Similarly, to deliver a desired component into the blood vessel, a syringe may be connected to the catheter and in fluid communication with a second lumen that is in turn in fluid communication with the interior of the blood vessel. Here also, the physician uses one hand to grasp the syringe body and the other hand to actuate the plunger to deliver the desired component into the blood vessel.

There are some drawbacks associated with manual inflation procedures such as the ones described. For example, each time the physician wants to adjust or change the location of the balloon in the artery she must use her hand alternatingly on the proximal end of the catheter for maneuvering the balloon to the desired location, and on the component delivery device or the expansion device for pressurizing or depressurizing the balloon. Rather than switching hands between the balloon catheter and the delivery or expansion device, it is desirable for the physician to be able to simultaneously control the component delivery or expansion pressure and the location of the balloon in the artery. This simultaneous control of position and component delivery or balloon expansion pressure is not possible for a single physician using present manual procedures. Another drawback of manual systems is that the physician may experience hand fatigue as a result of operating a delivery or expansion device for several cycles, each lasting several seconds, during an angioplasty procedure. Additionally, manual inflation devices are typically bulky than when compared with more fragile and delicate dilatation balloon catheters and the presence of such a bulky instrument is preferably to be avoided in the immediate area of an angioplasty procedure.

In recent years, automated devices have become known, including microprocessor controlled units wherein a microprocessor provides control signals to a drive unit which advances or retracts a syringe for purpose of expanding or deflating a balloon catheter. The drive unit can be made to follow a predetermined pressure output pattern, based on the pressure detected by a pressure transducer in fluid communication with the radiopaque expansion media, and an internal clock.

However, these conventional automated devices have limitations. First of all, the prior art automated devices generally do not incorporate a scheme for automatically or semi-automatically controlling delivery of desired components into the blood vessels being repaired. In addition, they do not take into account variations in individual catheter volume, nor do they take into consideration system compliance or individual catheter compliance characteristics. Another problem with prior art automated devices is that expansion times and pressure are generally not controlled by the physician as treatment is taking place.

What has been needed and heretofore unavailable is an automated system that frees the physician from difficulties of manual component delivery and balloon expansion and deflation, but accounts for individual differences in balloon catheters and provides feedback to the physician regarding component delivery and expansion/deflation. The present invention fulfills this need.

SUMMARY OF THE INVENTION

The invention is directed to a programmable manifold system for controlling pressure and fluid delivery in a catheter system for use in repairing a body lumen of a patient. In controlling pressure and fluid delivery, the system can regulate delivery of a fluid to an inflatable member of a catheter so that expansion and deflation of the inflatable member is controlled and can regulate delivery of a desired component through the catheter and into the body lumen being repaired.

The programmable manifold system accomplishes pressure and fluid management by employing a disposable manifold having multiple ports, a display console and a motor driver which are each controlled by a computer based program stored in a microprocessor that is housed within the system, and by employing one or more reservoirs which supply desired fluid or components that are contemplated to be controlled by the system.

In a preferred embodiment, the manifold has five ports, each comprising valves that are capable of opening and closing in response to a signal generated by a physician operating the system or to a signal originating from the controlling program itself, and one reservoir containing radiopaque solution which is utilized to both expand the inflatable member and facilitate viewing of the interior profile of the subject blood vessel. A first valve controls passage of the radiopaque solution to and from a syringe-like arrangement that is actuated by the motor driver. A second valve controls passage of the radiopaque solution to a lumen in fluid communication with the inflatable member of a catheter and a third valve controls passage of radiopaque solution into a lumen in fluid communication with the subject blood vessel. Finally, a fourth valve controls flow into the manifold from the radiopaque solution reservoir, whereas a fifth valve allows for purging system air. In addition, the preferred embodiment contemplates remote control of the programmable manifold, where the operator can conveniently control the position of the catheter and simultaneously control system pressure and fluid delivery.

It is also contemplated that the programmable manifold have the ability to perform desired functions automatically or where the system program controls the operation, and also perform the desired functions semi-automatically or where the operation of the system is capable of being adjusted or completely controlled remotely by an operator. By being able to perform automatically or semiautomatically, the programmable manifold system has greater flexibility, in that, it can perform without operator intervention in appropriate situations and also respond to operator commands when it is deemed necessary.

By controlling system pressure, the programmable manifold system operates to control the expansion and deflation of the inflatable member comprising the catheter. In order to control system pressure, the system senses and controls the rate of change of pressure within the inflatable member of a catheter, such that the inflatable member is expanded or deflated by radiopaque solution and pressurized at predetermined or preselected rates of increasing or decreasing pressure. Sensing and controlling the rate of change of pressure of the inflation media within the catheter system eliminates differences in catheter expansion characteristics due to differences in system volume and compliance.

By embodying fluid management capabilities, the programmable manifold has the ability to control delivery of media, and in the case of the preferred embodiment, of radiopaque solution to the repair site of a blood vessel. In addition, by possessing fluid management capabilities, the delivery of radiopaque solution to the repair site may be performed prior or subsequent to repair and can be repeated as necessary in order to obtain a sufficient view, through radiography, of the repair site.

In operation, the operator advances a catheter within a blood vessel and to the site of the blood vessel requiring repair. At this point, the operator may initiate a program which automatically controls an expansion and deflation sequence of the inflatable member of a catheter and that automatically controls delivery of radiopaque solution to the repair site. Alternatively, the physician may choose to retain control over the operation, whereby the operator sends signals to the programmable manifold system. In either case, a remote control may be utilized as the origin of preferred commands which are received and interpreted by a microprocessor so that desired functions are accomplished, thereby enabling the operator to conveniently adjust the position of the catheter as well as perform expansion or fluid delivery functions. In order to perform expansion or fluid delivery functions and upon interpreting a signal, the microprocessor relays the interpreted signal to the motor driver which in turn actuates the syringe unit, and also relays the interpreted signal to the manifold valves so that they open and close as necessary so as to perform the selected operation.

A typical operational sequence involves generating appropriate signals to open the valves to the radiopaque solution reservoir and the syringe unit and to activate the motor driver so that a plunger within the syringe unit is retracted and so that the syringe unit is filled to a desired level from the radiopaque solution reservoir. Thereafter, the motor is stopped and the valves are closed. Dependent upon the desired function, the valves leading to the inflatable member of the catheter or the valves leading to the lumen in fluid communication with the blood vessel may be opened so that the inflatable member may be expanded or the radiopaque fluid can be delivered to the blood vessel. Next, the valve to the syringe unit is opened and the motor driver activated to advance the plunger within the syringe structure so that the radiopaque solution flows to the desired location. Thereafter, the motor is stopped and all valves are closed. Where the inflatable member has been expanded, the system operates in reverse to deflate the inflatable member.

After operation of the programmable manifold system has been initiated, the microprocessor begins receiving information from pressure transducers regarding the actual pressure and/or radiopaque fluid delivered and compares the actual values with the expected and desired values based upon the predicted operation of the system. In response to detecting deviations from the expected values, the system adjusts motor speed so that, upon repeating an expansion or fluid delivery cycle, the actual values will match the expected values.

During the cycling of the expansion and/or fluid delivery cycles, the display console indicates the function currently being performed by the system, and may also indicate the expected and desired parameters and related actual values. The physician can reflect upon the indicated parameters in light of the progress regarding blood vessel repair and utilize the remote control to input appropriate signals to modify or end a cycle, thereby improving the effectiveness of the programmable manifold system. Once the physician or operator is satisfied that a blood vessel is fully repaired, the catheter can be removed from the patient and the programmable manifold system can be shut down.

In another embodiment, the programmable manifold system may have additional features such as separate reservoirs and manifold ports so that drugs or various flushing solutions may be delivered to the repair site. These features can easily be incorporated into the programmable manifold system and can similarly be performed automatically or semi-automatically. As an example, a therapeutic drug may be substituted for the radiopaque fluid and the inflatable member can have minute holes that allow the drug diffuse in a controlled manner when the inflatable member is pressurized as above-described. Other uses include performing medical procedures in peripheral areas of the body such as well know percutaneous transluminal angioplasty (PTA).

Other features and advantages of the present invention will become apparent from the following detailed description, taken in conjunction with the accompanying drawings, which illustrate, by way of example, the principles of the invention.

DETAILED DESCRIPTION

Figure 1:
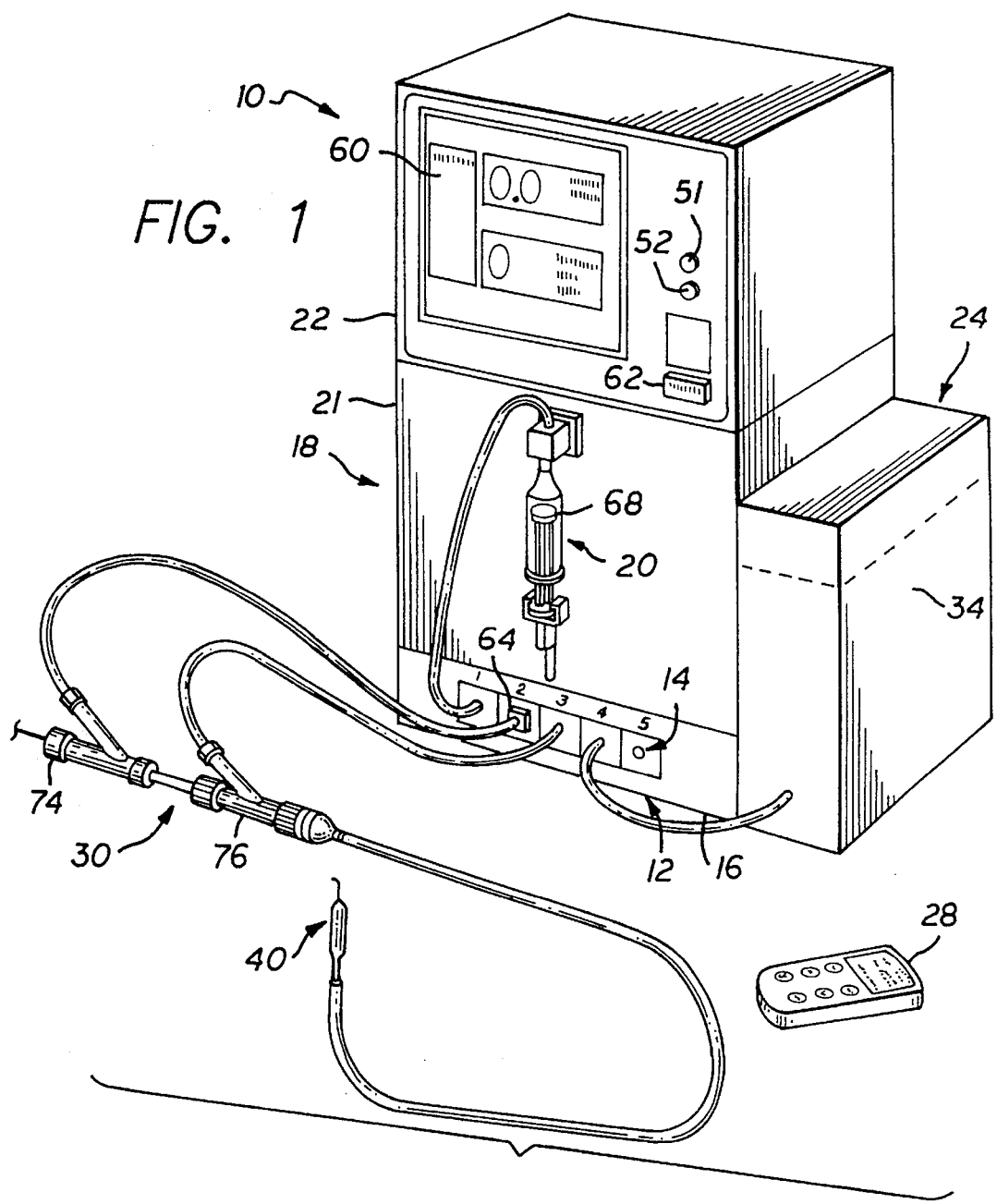
FIG. 1 is a schematic representation of a programmable manifold embodying features of the invention.

As shown in the drawings, which are included for purposes of illustration and not by way of limitation, the invention is embodied in a programmable manifold system (FIG. 1) for controlling pressure and fluid delivery in a catheter system for use in repairing a body lumen of a patient. In a typical situation, a dilatation catheter is introduced into the vascular system of a patient and is directed to a point near the repair site of a blood vessel. Once at the repair site, the inflatable or balloon portion of the catheter is expanded so as to restore patency of the blood vessel and a desired component is delivered into the blood vessel so as to facilitate observation of the repair site or to aid in repairing the blood vessel. By convention, balloon expansion and component delivery can be accomplished either manually or automatically. Conventional automatic and manual systems, however, have limitations in that they do not free the operator from difficulties of manual component delivery and inflation as well as account for individual differences in dilatation catheters and provide feedback to the operator regarding component delivery and expansion.

The present invention controls pressure and fluid delivery by regulating delivery of a medium to an inflatable member of a catheter so that expansion and deflation of the inflatable member is controlled and by regulating delivery of a desired component through the catheter and into the body lumen being repaired. The programmable manifold system of the present invention accomplishes pressure and fluid delivery control automatically or semi-automatically so as to free the operator of manual component delivery and, in addition, accounts for individual differences in balloon catheters as well as provides feedback regarding system performance.

The programmable manifold system 10 embodies a disposable manifold 12 having a plurality of ports 14 and that is contained within a manifold housing 16, a motor driver 18 that is capable of actuating a syringe unit 20 and that is attached to a motor driver housing 21, a display console 22, and a reservoir 24 that contains media to be controlled by the system 10. The system also embodies a microprocessor 26 (not shown) capable of driving the system 10 and storing a system program 27 (not shown) and that may be contained entirely within the manifold housing 16 or the motor driver housing 21 or may be distributed between both housings. Attached to the programmable manifold system 10 or in wireless communication therewith, is a remote controller 28 that enables the operator to run the system 10 remotely. In addition, a catheter 30 may be attached to the system 10 so that its operation may be controlled and so that upon placement within a patient's vascular system, a blood vessel 31 (not shown) may be repaired.

Figure 3:
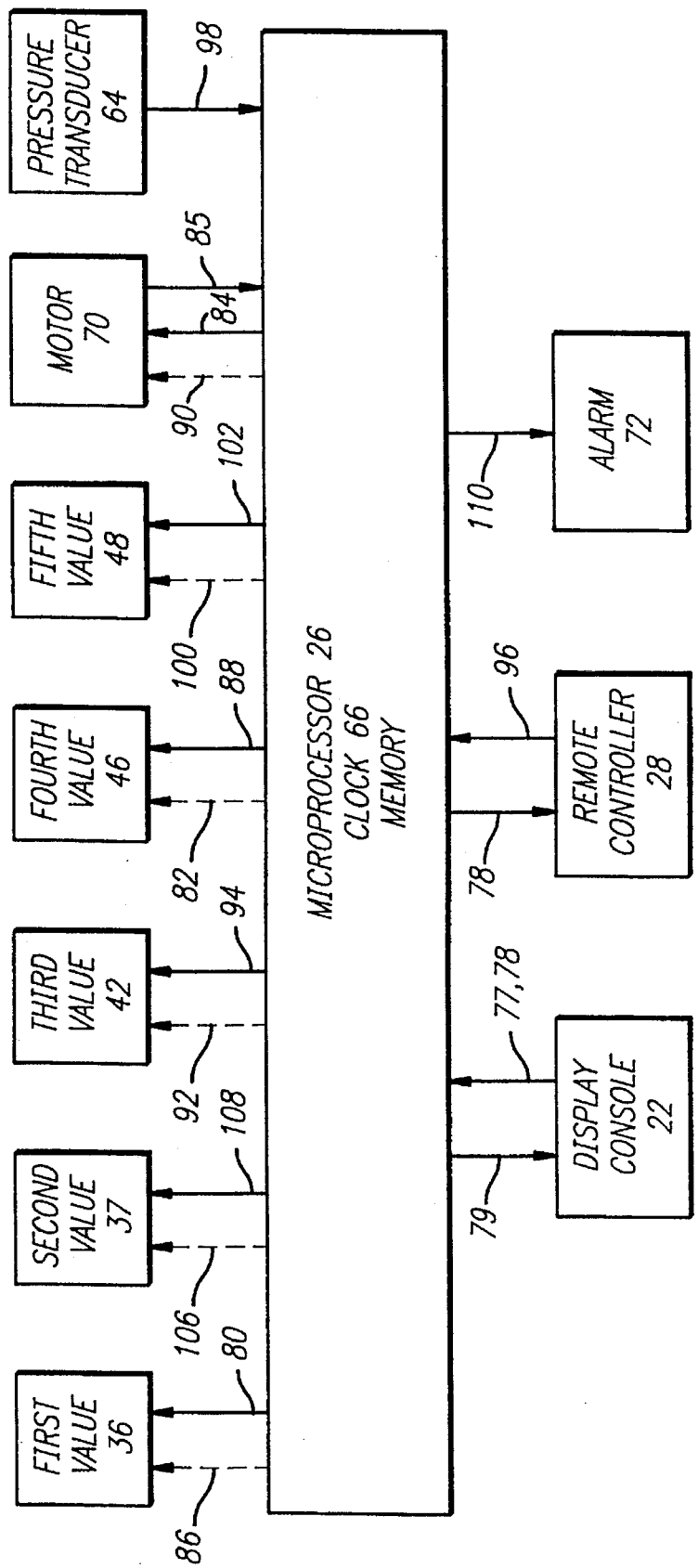
FIG. 3 is a functional block diagram that schematically illustrates the primary functions of a preferred embodiment of the invention.

In a preferred embodiment, it is contemplated that the manifold housing 16, the motor driver 18 and the display console 22 are in electronic communication with each other. It is also contemplated that the manifold 12 have five ports 14, each comprising valves that are capable of opening and closing in response to a signal generated by the system operator or to a signal originating from the system program 27. In addition, the preferred embodiment contemplates a reservoir 24 containing radiopaque solution 34 that supplies the programmable manifold system 10. A first valve 36 (see block representation of valves in FIG. 3) controls passage of radiopaque solution 34 to and from a syringe unit 20. A second valve 37 controls passage of radiopaque solution 34 to a catheter lumen, inflation lumen 38 (not shown), that is in fluid communication with an inflatable balloon 40 of a catheter 30. A third valve 42 controls passage of radiopaque solution 34 into a second catheter lumen, fluid delivery lumen 44 (not shown) that extends through the catheter 30 and that is in fluid communication with the blood vessel. A fourth valve 46 controls flow into the manifold 12 from the radiopaque solution reservoir 24. Finally, a fifth valve 48 is in fluid communication with the syringe unit 20 so that, when desired, air can be removed from the syringe unit 20.

Figure 2:
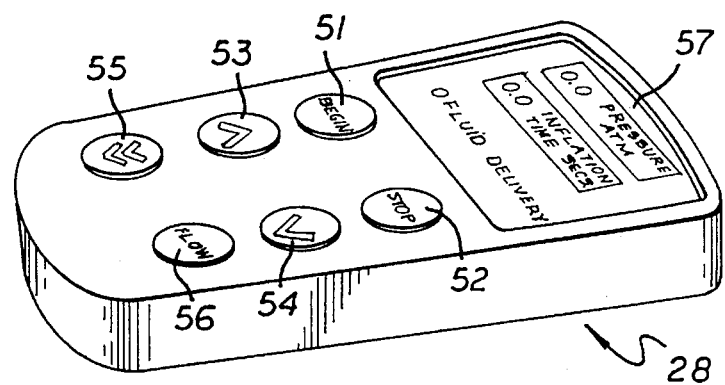
FIG. 2 is a schematic representation of a remote controller shown in FIG. 1.

Since it is contemplated that the programmable manifold system 10 free the operator of manual component delivery as well as perform automatically or semi-automatically, the system 10 comprises a remote controller 28 (FIG. 2), from which program initiating or altering signals may be generated. It is, therefore, contemplated that the remote controller 28 have a program initiation button 51 and a program cessation button 52 as well as an expansion button 53, a deflation button 54, a rapid deflation button 55 and a radiopaque delivery button 56. By depressing the program initiation button 51, the system program 27 commences and a desired automated sequence of balloon expansion and deflation and radiopaque solution delivery is performed, whereas depressing the program cessation button 52 stops the program or in the alternative, causes the system to return to a starting point. By depressing the expansion/deflation or delivery buttons 53, 54, 55, 56, the operator can effect the automated sequence or, when depressed after cessation or prior to commencing the program, full control of the programmable manifold system 10 can be in the operator.

It is also contemplated in a preferred embodiment that the operator be provided feedback regarding the performance of the system. In the preferred embodiment, the remote controller 28 may comprise a display 57 that indicates parameters which are critical to the function being performed, such as inflation time, system pressure and whether radiopaque solution 34 is being delivered. Similarly, the display console 22 is contemplated as indicating such critical parameters and also providing a menu 60 indicating the mode of operation. In addition, the display console 22 comprises a system power switch 62 and like the remote controller 28, the display console 22 provides means to initiate and stop the system program 27. The operator can, therefore, quickly determine from either the display console 22 or the remote controller 28 whether the system is performing as desired, and thereafter, make any necessary adjustments.

In order to provide the operator feedback concerning system pressure and expansion/deflation times, the programmable manifold system 10 employs a pressure transducer 64 that senses system pressure. The pressure transducer 64, in turn, generates a pressure signal that is interpreted by the system 10 and displayed in units of atmospheres. Upon commencement of balloon expansion or deflation, an internal clock 66 (not shown) begins to run and the time passed is displayed on the console 22 and the remote controller 28. In addition, the signal generated by the pressure transducer 64 is interpreted in light of desired atmospheric pressure values that are stored within the system program 27 and that are based upon pressure values expected to occur at specific times. Should the actual pressure value differ from the time-based desired value, the system 10 will automatically adjust by increasing or decreasing the rate at which a plunger 68 moves within the syringe unit 20, thereby compensating for differences in catheter inflation characteristics due to differences in catheter volume and compliance. In addition, a system may incorporate an expansion/deflation alarm 72 that signals the operator when the system 10 is unable to compensate for differences in catheter inflation characteristics and so that the operator can take control over the expansion/deflation process or abort the procedure.

In order to provide the operator feedback regarding delivery of media or, in the case of the preferred embodiment, radiopaque solution 34 into the blood vessel 31, the programmable manifold system 10 determines the volume of fluid dispensed by the syringe unit 20. To determine the volume of radiopaque solution 34 dispensed and by way of a tachometer 69 (not shown), the system 10 receives a signal generated by a motor 70 (not shown) regarding the number of revolutions of the motor 70, and by knowing the volume of the syringe unit 20 and the longitudinal travel of the plunger 68 within the syringe unit 20 as it corresponds to the number of motor revolutions, the motor generated signal can be interpreted by the system 10 and displayed in volume metric units.

In a typical operating sequence of a preferred embodiment (FIG. 3), the operator would attach a catheter 30 to the programmable manifold system 10 by connecting a dilatation catheter sidearm 74 in fluid communication with the second valve 37 of the manifold 12 and a right hand valve 76 in fluid communication with the third valve 42 of the manifold 12. The operator would then start the system by depressing the system power switch 62 located on the display console 22, which in turn sends a signal 77 to the microprocessor 26 so that the system 10 is turned on. Next, the operator may introduce the catheter 30 into a patient's vasculature and cause the catheter 30 to arrive at the repair site of a blood vessel 31.

At this point, the operator may choose to initiate an automatic sequence, whereby the operator depresses a button 51 on the remote controller 28 or the display console 22 which sends a signal 78 to the microprocessor 26 so that the automated system program 27 is initiated. The microprocessor 26 then begins to automatically generate signals at appropriate times as calculated by the system clock 66. At any time during the automated sequence, the operator may choose to have the system operate semi-automatically or to take full control of the operation of the programmable manifold system 10. In order to gain control, the operator need only generate signals from the remote controller 28, or from the display console 22. When operating automatically, the system 10 adjusts to operator commands and thereafter returns to a normal automatic operating sequence. In the alternative, when the system is operating semi-automatically, the system 10 simply responds to operator commands.

Whether or not the system is operating automatically or semi-automatically, the signals communicated within the system are the same. In order to deliver radiopaque solution 34 to the repair site, a signal 78 is generated from either the display console 22 or the remote controller 28 and the signal 78 is interpreted by the microprocessor 26. The microprocessor 26 in turn generates a signal 79 that is sent to the display console 22 so that the menu 60 on the display console 22 indicates that the system 10 is currently running a fluid delivery cycle. The system 10 also generates signals 80, 82 to the first valve 36 and the fourth valve 46 so that these valves are opened. By opening the first and fourth valves 36, 46, radiopaque solution 34 is allowed to travel from the radiopaque solution reservoir 24 through the fourth valve 46 and through the first valve 36 and into the syringe unit 20. Contemporaneous with sending signals to the first and fourth valves 36, 46, the system 10 generates a signal 84 that is sent to the motor driver 18 that, in turn, actuates longitudinal movement of the plunger 68 contained within the syringe unit 20 so that radiopaque solution 34 may be drawn into the syringe unit 20. In addition, and any time the motor driver 18 operates, a signal 85 is generated from the motor driver 18 to the microprocessor that is a function of the number of revolutions the motor 70 has completed. Next, the microprocessor sends signals 86, 88, 90 to the first valve 36, the fourth valve 46, and the motor driver 18, so that the valves are closed and the longitudinal movement of the plunger 68 is ceased.

At this point, the system 10 is ready to deliver fluid through a fluid delivery lumen 44 that is in fluid communication with the interior of the blood vessel 31 being repaired and by delivering the radiopaque solution 34 to the repair site in this way, the operator can, through radiography, observe the internal profile of a blood vessel. The system 10 then generates signals 84, 80, 92 to the motor driver 18, to the first valve 36 and to the third valve 42 respectively so that the valves are opened and so that the syringe unit 20 delivers radiopaque solution 34 through the catheter 30 and into the blood vessel 31. Thereafter, the system 10 generates signals 86, 94, 90 to close the valves and stop the motor driver 18 as well as indicate on the display console 22 and remote controller 28 that the delivery cycle has been performed and has been completed.

In order to expand and deflate the inflatable member 40, the system 10 extracts fluid from the radiopaque solution reservoir 24 and delivers it to the inflatable member 40, all the while sensing system pressure by way of a pressure transducer 64. As with fluid delivery to the blood vessel, whether or not the system is performing automatically or semi-automatically, the signals communicated within the system are the same.

It may be desirable to first prep a catheter 30, prior to use in repairing a blood vessel 31. To do so, the system 10 generates signals 80, 106, 84 so that the first valve 36 and the second valve 37 are opened and so that the motor driver 18 causes the plunger 68 within the syringe unit 20 to withdraw all air within the catheter 30 so as to create a vacuum within the catheter 30. The system then send signals 86, 106, 90 to close valves and cease operation of the motor driver 18. Thereafter, signals 80, 100, 84 are generated to open the first and fifth valves 36, 48 and to cause the motor driver 18 to force the extracted air from the syringe unit 20 and out of the fifth valve 48. Next, signals 86, 102, 90 are transmitted so that the valves are closed and the operation of the motor driver 18 is ceased.

Subsequent to creating a vacuum within the catheter 30, signals 82, 106, 88, 108 are transmitted to open the second and fourth valves 37, 46 so that the vacuum within the catheter 30 draws radiopaque solution 34 into the catheter 30 and to then close the valves. Thereafter, additional signals 80, 82, 85 are generated so that the first and fourth valves 36, 46 are opened and so that the motor driver 18 is actuated and causes the syringe unit 20 to withdraw radiopaque fluid from the reservoir 24 and into the syringe unit 20. Next, the system 10 sends signals 86, 88, 90 to close the valves and stop the motor driver as well as receives signals 85, 90 from the motor driver 18 regarding the number of revolutions completed by the motor 70 and from the pressure transducer 64 regarding system pressure. The signals 85, 98 received from the motor driver 18 and the pressure transducer 64 are in turn continuously interpreted and translated into volumetric values and atmospheres respectively and are stored within the microprocessor 26.

Signals are then transmitted to open the first and second valves 36, 37 to the motor driver 18 so that the radiopaque solution 34 contained within the syringe unit 20 can be delivered through inflation lumen 38 and to the inflatable member 40, so as to create a desired pressure within the catheter 30. An expected system pressure based upon the known amount of radiopaque solution 34 delivered to the catheter 30 is compared with the actual system pressure as sensed by the pressure transducer 64 and the system quickly responds by increasing or decreasing the rate at which radiopaque solution 34 is introduced into the catheter 30, thereby adjusting for differences in volumetric capacity and compliance from one catheter to another. (It should be noted that these system adjustments regarding catheter differences can be made prior to placing the catheter within the patient's vasculature.) In addition, the microprocessor 26 transmits signals to the remote controller 28 and the display console 22 during this process so as to provide the operator with knowledge of the systems pressure. The microprocessor 26 also observes system pressure and should the system not be able to adjust appropriately, a signal 110 is transmitted to set off an alarm so as to alert the operator. Finally, once the inflatable member 40 is expanded to the desired degree, the system can deflate the inflatable member 40 by generating signals that reverse the process and then repeat expansion and deflation cycles as necessary.

It is also contemplated that the preferred embodiment comprise means to manually override the system 10 should the system 10 not perform as desired or where it is necessary to react quicker than the system 10 is capable of performing. Therefore, it is contemplated the plunger 68 can be manually activated so as to allow the operator to deliver radiopaque solution 34 to or withdraw radiopaque solution 34 from the system 10.

In another embodiment (not shown) the programmable manifold system 10 may have additional ports 14 each having valves that open and close in response to system generated signals that control passage of fluid from additional reservoirs to the syringe unit 20. Where the system is so configured, other components such as drugs or flushing solutions, may, when desired, be delivered to the blood vessel 30. The operation of such a system would be similar to that of the preferred embodiment, in that, the microprocessor would transmit signals to control these additional valves and the system could perform automatically or semi-automatically. In addition, it is also contemplated that catheter 30 comprises a lumen that is capable of acting both as a conduit for fluid delivery as well as a conduit for expanding the inflatable member 40, wherein the inflatable member 40 has minute holes through which fluid may be delivered to the blood vessel 31. In such a catheter, desired fluids may be delivered to the patient's vasculature in a controlled manner and also used to expand the inflatable member.

While particular forms of the invention have been illustrated and described, it will be apparent that various modification can be made without departing from the spirit and scope of the invention. Thus, it should be understood that various changes in form, detail and application of the present invention may be made without departing from the spirit and scope of this invention.

What is claimed is:

1. An automatic fluid delivery system, comprising:
    a manifold having a plurality of ports, each port including a valve for controlling the flow of fluid therethrough;
    a fluid drive means for drawing fluid from and delivering fluid to said manifold via a first one of said ports;
    a catheter in fluid communication with said manifold via a second one of said ports;
    a fluid reservoir in fluid communication with said manifold via a third one of said ports; and
    means for controlling said valves and said fluid drive means to coordinate their operation to cause fluid from said reservoir to flow into said catheter through said manifold.

2. The automatic fluid delivery system of claim 1 wherein a fourth one of said ports is vented to the atmosphere, and wherein said controlling means are operative to coordinate the operation of said valves and said fluid drive means to purge air from the system through said fourth port.

3. The automatic fluid delivery system of claim 1 wherein the operation of said controlling means is programmable.

4. The automatic fluid delivery system of claim 1 wherein the controlling means is also for coordinating the operation of the valves and the fluid drive means to pressurize the fluid in the catheter.

5. The automatic fluid delivery system of claim 4 further comprising a pressure transducer in fluid communication with the catheter operative to provide a signal to said controlling means indicative of pressure within said catheter.

6. The automatic fluid delivery system of claim 5 wherein said controlling means is programmed to vary the pressure within said catheter at a predetermined rate.

7. The automatic fluid delivery system of claim 1 wherein:
    the catheter comprises an inflatable balloon;
    the controlling means is also for coordinating the operation of the valves and the fluid drive means to pressurize the fluid in the catheter to control the inflation of the balloon.

8. The automatic fluid delivery system of claim 7 further comprising a pressure transducer in fluid communication with the balloon of the catheter operative to provide a signal to said controlling means indicative of pressure within said balloon;
    wherein said controlling means is programmed to vary the pressure within said balloon at a predetermined rate.

9. The automatic fluid delivery system of claim 1 further comprising:
    an infusion catheter in fluid communication with said manifold via a fifth one of said ports; and
    means for measuring the volume of fluid passing through said manifold;
    wherein said controlling means coordinates the operation of said valves and said drive means to deliver a predetermined volume of fluid contained in said reservoir to said infusion catheter at a predetermined rate.

10. An automatic fluid delivery system, comprising:
    a manifold having a plurality of ports, each including a valve for controlling the flow of fluid therethrough;

a fluid drive means for drawing fluid from and delivering fluid to said manifold via a first one of said ports;

a balloon catheter in fluid communication with said manifold via a second one of said ports;

a fluid reservoir in fluid communication with said manifold via a third one of said ports; and means for controlling said valves and said fluid drive means to coordinate their operation to cause fluid from said reservoir to pressurize said balloon catheter through said manifold.

11. The automatic fluid delivery system of claim 10 wherein a fourth one of said ports is vented to the atmosphere, and wherein said controlling means are operative to coordinate the operation of said valves and said fluid drive means to purge air from the system through said fourth port.

12. The automatic fluid delivery system of claim 10 wherein the operation of said controlling means is programmable.

13. The automatic fluid delivery system of claim 12 further comprising a pressure transducer operative to provide a signal to said controlling means indicative of the pressure within said balloon catheter.

14. The automatic fluid delivery system of claim 13 wherein said controlling means is programmed to vary the pressure within said catheter at a predetermined rate.

15. The automatic fluid delivery system of claim 10 further comprising:

an infusion catheter in fluid communication with said manifold via a fifth one of said ports;

means for measuring the volume of fluid passing through said manifold; and wherein said controlling means coordinates the operation of said valves and said drive means to deliver a predetermined volume of fluid contained in said reservoir to said infusion catheter at a predetermined rate.

16. An automatic fluid delivery system, comprising:

a manifold having a plurality of ports, each port including a valve for controlling the flow of fluid therethrough;

a fluid drive means for drawing fluid from and delivering fluid to said manifold via a first one of said ports;

an inflatable balloon catheter in fluid communication with said manifold via a second one of said ports;

a fluid reservoir in fluid communication with said manifold via a third one of said ports; and means for controlling said valves and said fluid drive means to coordinate their operation to cause fluid from said reservoir to flow into said catheter through said manifold and to apply controllable pressure to the inflatable balloon to control its inflation; and a pressure transducer in fluid communication with the balloon of the catheter operative to provide a signal to said controlling means indicative of pressure within said balloon;

wherein said controlling means is programmed to vary the pressure within said balloon at a predetermined rate.

17. The automatic fluid delivery system of claim 16 wherein a fourth one of said ports is vented to the atmosphere, and wherein said controlling means are operative to coordinate the operation of said valves and said fluid drive means to purge air from the system through said fourth port.

* * * * *